US012653818B2

(12) United States Patent
Liu et al.

(10) Patent No.: US 12,653,818 B2

(45) Date of Patent: Jun. 16, 2026

(54) PHARMACEUTICAL COMPOSITIONS COMPRISING NITROXOLINE LYSINATE, PREPARATION METHOD THEREFOR AND USE THEREOF

(71) Applicants: Jiangsu Yahong Meditech Co., Ltd., Taizhou (CN); Asieris Pharmaceuticals (Shanghai) Co., Ltd., Shanghai (CN)

(72) Inventors: Jianghua Liu, Taizhou (CN); Ke Pan, Shanghai (CN); Yushen Guo, Shanghai (CN); Shuai Shen, Taizhou (CN); Jili Sun, Taizhou (CN); Dandan Li, Taizhou (CN); Jie Chen, Taizhou (CN)

(73) Assignees: Jiangsu Yahong Meditech Co., Ltd., Taizhou (CN); Asieris Pharmaceuticals (Shanghai) Co., Ltd., Shanghai (CN)

( * ) Notice: Subject to any disclaimer, the term of this patent is extended or adjusted under 35 U.S.C. 154(b) by 687 days.

(21) Appl. No.: 18/002,932

(22) PCT Filed: May 26, 2021

(86) PCT No.: PCT/CN2021/096041

§ 371 (c)(1),
(2) Date: Dec. 22, 2022

(87) PCT Pub. No.: WO2022/001512

PCT Pub. Date: Jan. 6, 2022

(65) Prior Publication Data

US 2023/0248716 A1 Aug. 10, 2023

(30) Foreign Application Priority Data

Jul. 3, 2020 (CN) ......................... 202010635876.9

(51) Int. Cl.

| | |
|---|---|
| *A61K 31/47* | (2006.01) |
| *A61K 9/20* | (2006.01) |
| *A61K 9/24* | (2006.01) |
| *A61K 9/28* | (2006.01) |
| *A61K 47/12* | (2006.01) |
| *A61K 47/32* | (2006.01) |
| *A61K 47/38* | (2006.01) |

(52) U.S. Cl.

CPC .............. *A61K 31/47* (2013.01); *A61K 9/209* (2013.01); *A61K 9/2095* (2013.01); *A61K 9/2866* (2013.01); *A61K 47/12* (2013.01); *A61K 47/32* (2013.01); *A61K 47/38* (2013.01)

(58) Field of Classification Search

CPC ...................................................... A61K 31/47

See application file for complete search history.

(56) References Cited

U.S. PATENT DOCUMENTS 9,758,484 B2 * 9/2017 Pan ......................... A61P 13/02

FOREIGN PATENT DOCUMENTS

| | | | | |
|---|---|---|---|---|
| CN | 105228984 | * | 1/2015 | ................ A61P 9/00 |
| CN | 105228984 A | | 1/2016 | |
| CN | 111773193 A | | 10/2020 | |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*

"Find ETDs Home >> Thesis Resources >> Find ETDs" Online: "https://ndltd.org/thesis-resources/find-etds/" Accessed Jan. 31, 2023.*

Irwin "Zinc—A Free Database of Commercially Available Compounds for Virtual Screening" J. Chem. Inf. Model. 2005, 45, 177-182.*

Kim "PubChem in 2021: new data content and improved web interfaces" Nucleic Acids Research, 2021, vol. 49, Database issue Published online Nov. 5, 2020.*

STN Registry/Zregistry (CAS Registrysm) Sep. 2016 2 pages.*

Kawakami, Suppression of pancreatic fistula using drugs—Verification using a rat pancreatic fistula model, Abstracts of the Annual Congress of Japan Surgical Society, 117:2037 (2017).*

Yang, Chinese Pharmaceutical Journal, 46(23), 2011.*

Rowe, Handbook of Pharmaceutical Excipients, Sixth Edition, 2009.*

Kerns, Drug-like Properties:Concepts, Structure Design and Methods, Academic Press, 2008.*

International Search Report issued Aug. 30, 2021 in PCT/CN2021/096041.

Yang, Meiyan, et al., Non-official translation: "Research Progress on Biphasic Drug Delivery System of Bilayer Tablets," Chinese Pharmaceutical Journal, vol. 46, No. 23, Dec. 8, 2011.

* cited by examiner

*Primary Examiner* — Nizal S Chandrakumar

(74) *Attorney, Agent, or Firm* — ICE MILLER LLP

(57) ABSTRACT

Pharmaceutical compositions comprising nitroxoline lysinate, a preparation method therefor and a use thereof. The pharmaceutical compositions comprise a first layer and a second layer. The first layer comprises, based on the total weight of the first layer, 40%-70% of active pharmaceutical ingredient, 10%-30% of filler, 5%-12% of disintegrant, 0.5%-2% of lubricant, 0.1%-1.5% of glidant and 10%-20% of alkaline substance. The second layer comprises, based on the total weight of the second layer, 40%-70% of active pharmaceutical ingredient, 10%-30% of filler, 10%-35% of sustained-release material, 0.1%-2% of lubricant and 0.1%-2% of glidant. The active pharmaceutical ingredient is selected from one or more of nitroxoline lysinate, nitroxoline lysinate crystalline form and nitroxoline lysinate solvate. The pharmaceutical compositions can achieve the purpose of burst release at an early stage and sustained and slow release at a later stage.

20 Claims, 3 Drawing Sheets

PHARMACEUTICAL COMPOSITIONS COMPRISING NITROXOLINE LYSINATE, PREPARATION METHOD THEREFOR AND USE THEREOF

CROSS-REFERENCE TO RELATED APPLICATION

This application is a Section 371 of International Application No. PCT/CN2021/096041 filed May 26, 2021, which was published in the Chinese language Jan. 6, 2022, under International Publication No. WO 2022/001512 A1, which claims priority to Chinese Patent Application No. 202010635876.9 filed Jul. 3, 2020, the disclosures of which are incorporated herein by reference in their entireties.

FIELD OF THE INVENTION

The present invention relates to a pharmaceutical composition comprising nitroxoline lysinate, a method for preparing the same, and a use thereof.

BACKGROUND OF THE INVENTION

Nitroxoline, the chemical name of which is 5-nitro-8-hydroxyquinoline, was developed as an oral antibiotic drug in the 1960s. It was mainly used for urinary system infections and had a relatively safe history of use before being replaced due to discovery and use of new antibiotics.

In recent years, new studies have found that nitroxoline can simultaneously inhibit the methionine aminopeptidase MetAP2 and the silence information regulator 2-related enzyme SIRT1 in vascular endothelial cells, exerting a synergistic inhibitory effect on tumor angiogenesis, as well as an inhibitory effect on the proliferation of tumor cells. Therefore, nitroxoline has been re-developed to treat tumors including bladder cancer.

However, it is a problem to be solved in the art to improve the water solubility of nitroxoline, thereby improving its druggability and activity.

Example 18 of the patent application publication No. CN 105228984 A (published on 6 Jan. 2016) discloses a nitroxoline lysinate and a method for preparing the same, the water solubility of the nitroxoline lysinate is better than that of nitroxoline. However, in the prior art, there are no nitroxoline lysinate-containing pharmaceutical compositions, such as formulations.

SUMMARY OF THE INVENTION

The present inventor has developed a pharmaceutical composition for nitroxoline lysinate through intensive research. The pharmaceutical composition has good dissolution properties, and can achieve the purpose of burst release in the early stage and sustained slow release in the later stage.

Therefore, the present invention provides a nitroxoline lysinate-containing pharmaceutical composition, comprising a first layer and a second layer;

the first layer comprises 40% to 70% of an active pharmaceutical ingredient, 10% to 30% of a filler, 5% to 12% of a disintegrant, 0.5% to 2% of a lubricant, 0.1% to 1.5% of a glidant and 10% to 20% of an alkaline substance by weight, relative to the total weight of the first layer; the second layer comprises 40% to 70% of an active pharmaceutical ingredient, 10% to 30% of a filler, 10% to 35% of a sustained release material, 0.1% to 2% of a lubricant and 0.1% to 2% of a glidant by weight, relative to the total weight of the second layer; and the active pharmaceutical ingredient in the first layer and the second layer is one or more independently selected from the group consisting of nitroxoline lysinate, a crystal form of nitroxoline lysinate, and a solvate of nitroxoline lysinate.

In the above pharmaceutical composition, the structural formula of the nitroxoline lysinate is as follows:

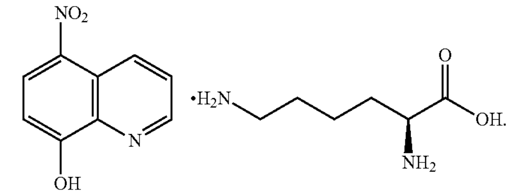

In the above pharmaceutical composition, the active pharmaceutical ingredient is preferably a solvate of nitroxoline lysinate, more preferably a hydrate of nitroxoline lysinate, and further more preferably nitroxoline lysinate monohydrate. The structural formula of the nitroxoline lysinate monohydrate is

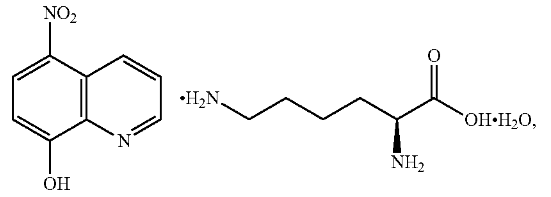

and the nitroxoline lysinate monohydrate can be prepared by the preparation method of Example 18 of the patent publication application No. CN 105228984 A (published on 6 Jan. 2016).

In the above pharmaceutical composition, the active pharmaceutical ingredient in the first layer is preferably present in an amount of 40% to 60%, more preferably 55% to 57%, and most preferably 56% by mass, relative to the mass of the first layer.

In the above pharmaceutical composition, the filler in the first layer can be one or more of microcrystalline cellulose, starch, lactose monohydrate and calcium hydrogen phosphate, preferably microcrystalline cellulose or starch, and more preferably microcrystalline cellulose.

In the above pharmaceutical composition, the filler in the first layer is preferably present in an amount of 15% to 30%, more preferably 19% to 20%, and most preferably 19.5% by mass, relative to the mass of the first layer.

In the above pharmaceutical composition, the disintegrant in the first layer can be one or more of crospovidone, sodium carboxymethyl starch, low-substituted hydroxypropylcellulose and sodium croscarmellose, preferably crospovidone or sodium carboxymethyl starch, and more preferably crospovidone.

In the above pharmaceutical composition, the disintegrant in the first layer is preferably present in an amount of 7% to 12%, more preferably 7.5% to 8.5%, and most preferably 8% by mass, relative to the mass of the first layer.

In the above pharmaceutical composition, the lubricant in the first layer can be one or more of magnesium stearate, stearic acid and sodium lauryl sulfate, preferably magnesium stearate or stearic acid, and more preferably magnesium stearate.

In the above pharmaceutical composition, the lubricant in the first layer is preferably present in an amount of 0.5% to 1.5%, and most preferably 1% by mass, relative to the mass of the first layer.

In the above pharmaceutical composition, the glidant in the first layer can be one or two of micronized silica gel and talc, and preferably micronized silica gel.

In the above pharmaceutical composition, the glidant in the first layer is preferably present in an amount of 0.2% to 1%, and most preferably 0.5% by mass, relative to the mass of the first layer.

In the above pharmaceutical composition, the alkaline substance in the first layer can be one or two of sodium bicarbonate and sodium carbonate, and preferably sodium bicarbonate.

In the above pharmaceutical composition, the alkaline substance in the first layer is preferably present in an amount of 14% to 20%, more preferably 14% to 16%, and most preferably 15% by mass, relative to the mass of the first layer.

In the above pharmaceutical composition, the active pharmaceutical ingredient in the second layer is preferably present in an amount of 50% to 60%, more preferably 55% to 57%, and most preferably 56% by mass, relative to the mass of the second layer.

In the above pharmaceutical composition, the filler in the second layer can be one or more of microcrystalline cellulose, starch, lactose monohydrate and calcium hydrogen phosphate, preferably lactose monohydrate or microcrystalline cellulose, and more preferably lactose monohydrate.

In the above pharmaceutical composition, the filler in the second layer is preferably present in an amount of 16% to 30%, more preferably 17% to 19%, and most preferably 18% by mass, relative to the mass of the second layer.

In the above pharmaceutical composition, the sustained release material in the second layer can be one or two of hydroxypropyl methylcellulose and xanthan gum, preferably hydroxypropyl methylcellulose, more preferably one or more of hydroxypropyl methylcellulose K4M, hydroxypropyl methylcellulose K15M and hydroxypropyl methylcellulose K100M, and further more preferably hydroxypropyl methylcellulose K4M.

In the above pharmaceutical composition, the sustained release material in the second layer is preferably present in an amount of 19% to 35%, more preferably 24% to 26%, and most preferably 25% by mass, relative to the mass of the second layer.

In the above pharmaceutical composition, the lubricant in the second layer can be one or more of magnesium stearate, stearic acid and sodium lauryl sulfate, preferably magnesium stearate or stearic acid, and more preferably magnesium stearate.

In the above pharmaceutical composition, the lubricant in the second layer is preferably present in an amount of 0.2% to 1%, and most preferably 0.5% by mass, relative to the mass of the second layer.

In the above pharmaceutical composition, the glidant in the second layer can be one or two of micronized silica gel and talc, and preferably micronized silica gel.

In the above pharmaceutical composition, the glidant in the second layer is preferably present in an amount of 0.2% to 1%, and most preferably 0.5% by mass, relative to the mass of the second layer.

In the above pharmaceutical composition, the mass ratio of the first layer to the second layer is preferably 1:3 to 2:1, more preferably 1:2 to 1:1.5, and most preferably 1:2. The mass ratio of the first layer to the second layer can make the resulting pharmaceutical composition have good pharmacokinetic characteristics advantageously useful for the preparation of drugs, and have a good clinical application prospect.

In the above pharmaceutical composition, the pharmaceutical composition can also comprise a coating agent. The coating agent can be a coating agent commonly used in the art, for example, a coating agent whose trade name is Opadry. The coating agent can be present in an amount commonly used in the art, for example, the ratio of the mass of the coating agent to the mass of the uncoated pharmaceutical composition is 2% to 4%.

In the above pharmaceutical composition, the pharmaceutical composition can also comprise one or more of colorant, pH adjuster, surfactant, stabilizer and fragrance.

The pharmaceutical composition of the present invention can be in a conventional dosage form in the art, such as a solid formulation, such as a granule, powder or tablet, preferably a tablet, more preferably a sustained release tablet, such as an oral tablet or an oral sustained release tablet.

The present invention also provides a nitroxoline lysinate-containing formulation comprising a first layer and a second layer; wherein the first layer comprises 40% to 70% of an active pharmaceutical ingredient, 10% to 30% of a filler, 5% to 12% of a disintegrant, 0.5% to 2% of a lubricant, 0.1% to 1.5% of a glidant and 10% to 20% of an alkaline substance by weight, relative to the total weight of the first layer; the second layer comprises 40% to 70% of an active pharmaceutical ingredient, 10% to 30% of a filler, 10% to 35% of a sustained release material, 0.1% to 2% of a lubricant and 0.1% to 2% of a glidant by weight, relative to the total weight of the second layer; and the active pharmaceutical ingredient in the first layer and the second layer is one or more independently selected from the group consisting of nitroxoline lysinate, a crystal form of nitroxoline lysinate, and a solvate of nitroxoline lysinate, preferably a hydrate of nitroxoline lysinate, and more preferably nitroxoline lysinate monohydrate;

in the first layer, the filler is one or more of microcrystalline cellulose, starch, lactose monohydrate and calcium hydrogen phosphate, the disintegrant is one or more of crospovidone, sodium carboxymethyl starch, low-substituted hydroxypropylcellulose and sodium croscarmellose, the lubricant is one or more of magnesium stearate, stearic acid and sodium lauryl sulfate, the glidant is one or two of micronized silica gel and talc, and the alkaline substance is one or two of sodium bicarbonate and sodium carbonate;

in the second layer, the filler is one or more of lactose monohydrate, microcrystalline cellulose, starch and calcium hydrogen phosphate, the sustained release material is one or two of hydroxypropyl methylcellulose and xanthan gum, the lubricant is one or more of magnesium stearate, stearic acid and sodium lauryl sulfate, and the glidant is one or two of micronized silica gel and talc.

In the above formulation, the formulation is preferably a tablet, and more preferably a sustained release tablet.

In the above formulation, preferably, in the first layer, the filler is microcrystalline cellulose, the disintegrant is crospovidone, the lubricant is magnesium stearate, the glidant is micronized silica gel, and the alkaline substance is sodium bicarbonate; in the second layer, the filler is lactose monohydrate, the sustained release material is hydroxypropyl methylcellulose K4M, the lubricant is magnesium stearate, and the glidant is micronized silica gel. More preferably, the mass ratio of the first layer to the second layer is 1:3 to 2:1, preferably 1:2 to 1:1.5, and more preferably 1:2. The materials in the first layer and the second layer and the mass ratio of the first layer to the second layer can make the resulting formulation have good pharmacokinetic characteristics advantageously useful for the preparation of drugs, and have a good clinical application prospect.

The present invention also provides a preparation method for the aforementioned nitroxoline lysinate-containing pharmaceutical composition, comprising the following steps of:

1) mixing the remaining components of the first layer except the lubricant and the glidant, and subjecting the resulting mixture to wet granulation to obtain granule I; mixing the granule I with the lubricant and the glidant of the first layer to obtain the granules of the first layer;
2) mixing the remaining components of the second layer except the lubricant and the glidant, and subjecting the resulting mixture to wet granulation to obtain granule II; mixing the granule II with the lubricant and the glidant of the second layer to obtain the granules of the second layer;
3) compressing the granules of the first layer to obtain the first layer, and compressing the granules of the second layer on the top of the first layer to obtain the pharmaceutical composition; or, compressing the granules of the second layer to obtain the second layer, and compressing the granules of the first layer on the top of the second layer to obtain the pharmaceutical composition.

In the above preparation method, the wet granulation can be carried out according to common ways in the art, and generally comprises mixing the remaining components of the first or the second layer except the lubricant and the glidant with ethanol in water to obtain a soft material, sieving, drying and milling. The mass fraction of the ethanol in water is preferably 70 wt % to 80 wt %, for example, 75 wt %.

The present invention further provides a use of the aforementioned nitroxoline lysinate-containing pharmaceutical composition or the nitroxoline lysinate-containing formulation in the preparation of a medicament for treating an infectious disease or cancer. The infectious disease is preferably urinary tract infection. The cancer is preferably bladder cancer.

The pharmaceutical composition of the present invention can be administered to mammals, preferably humans, at a dose of 280 mg/tablet (equivalent to 150 mg of nitroxoline) twice a day, 2 tablets each time.

On the basis of not violating common knowledge in the art, the aforementioned preferred features can be combined arbitrarily to obtain preferred embodiments of the present invention.

The reagents and raw materials used in the present invention are all commercially available.

The positive progressive effects of the present invention are that: the pharmaceutical composition of the present invention has good dissolution properties, and can achieve the purpose of burst release in the early stage (0 to 2 hours) and sustained slow release in the later stage (2 to 12 hours) through the combination of drug release properties in different layers.

DETAILED DESCRIPTION OF THE INVENTION

Figure 1:
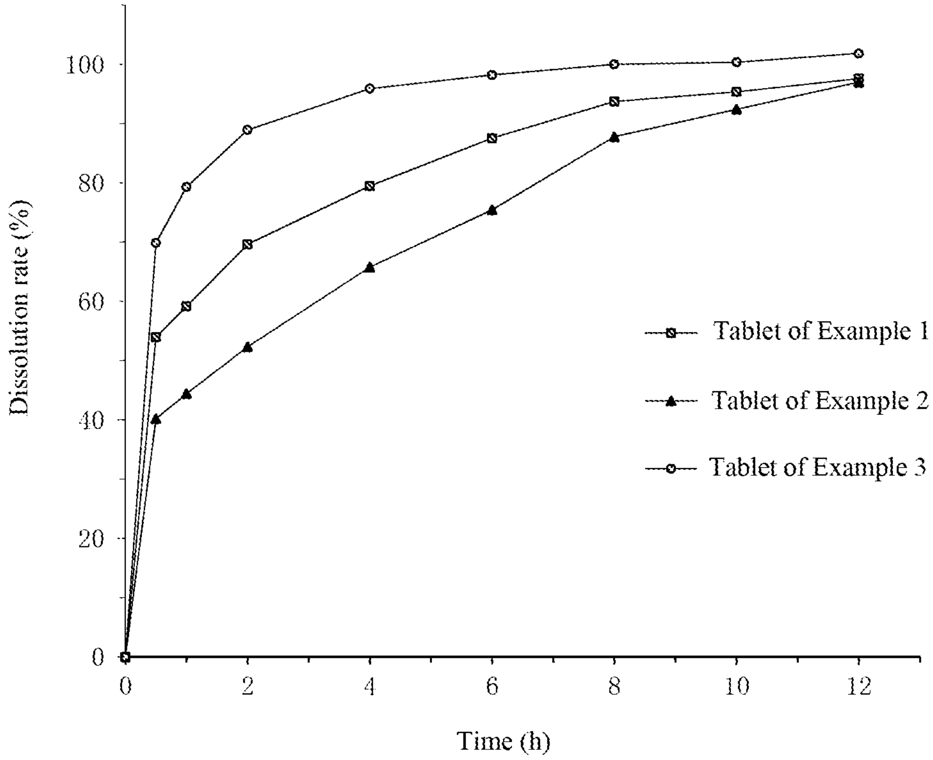
FIG. 1 is the dissolution profile of the tablets prepared in Examples 1 to 3 in PBS (pH 6.8).

The present invention will be described in detail below with reference to the Examples. The Examples of the present invention are only used to illustrate the technical solutions of the present invention, without limiting the essence and scope of the present invention.

In the following Examples, the active pharmaceutical ingredient refers to nitroxoline lysinate monohydrate, its chemical name is 5-nitro-8-hydroxyquinoline L-lysinate monohydrate, and its structural formula is:

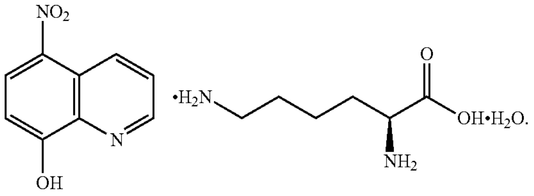

In the following Examples, the experimental reagents are as follows:

| Reagent | Source | Batch number |
|---|---|---|
| Active pharmaceutical ingredient | Obtained with reference to the preparation method of Example 18 of patent application CN201480025681.5 | / |
| Microcrystalline cellulose | Asahi Kasei, Japan | 22C1 |
| Sodium bicarbonate | Nanjing Chemical Reagent Co., Ltd. | 13081311235 |
| Crospovidone | International Specialty Products Inc., USA | 03900233886 |
| Micronized silica gel | Cabot | M5P |
| Magnesium stearate | PETER GREVEN, Netherlands | C804435 |
| Hydroxypropyl methylcellulose-K4M | Shanghai Colorcon | 2C26012N02 |
| Lactose monohydrate | Meggle GmbH, Germany | L1333A |

In the following Examples, the components and their amounts in the first layer and the second layer are as follows:

| Tablet | Function | Component | Example 1-3 | 4 | 5 | 6 | 7 | 8 |
|---|---|---|---|---|---|---|---|---|
| | | | Mass percentage/% | | | | | |
| First layer | Active pharmaceutical ingredient | 5-Nitro-8-hydroxyquinoline L-lysinate monohydrate | 56 | 54.5 | 54.4 | 40 | 70 | 56 |
| | Filler | Microcrystalline cellulose | 19.5 | 10 | 30 | / | / | / |
| | | Starch | / | / | / | / | 10 | / |
| | | Lactose monohydrate | / | / | / | 30 | / | / |
| | | Calcium hydrogen phosphate | / | / | / | / | / | 19.5 |
| | Disintegrant | Crospovidone | 8 | 12 | 5 | / | / | / |
| | | Sodium carboxymethyl starch | / | / | / | / | 5 | / |
| | | Low substituted hydroxypropyl cellulose | / | / | / | 12 | / | / |
| | | Croscarmellose sodium | / | / | / | / | / | 8 |
| | Lubricant | Magnesium stearate | 1 | 2 | 0.5 | / | / | 1 |
| | | Stearic acid | / | / | / | / | 0.5 | / |
| | | Sodium dodecyl sulfate | / | / | / | 2 | / | / |
| | Glidant | Micronized silica gel | 0.5 | 1.5 | 0.1 | / | / | 0.5 |
| | | Talc | / | / | / | 1.5 | 1.5 | / |
| | Alkaline substance | Sodium bicarbonate | 15 | 20 | 10 | / | / | 15 |
| | | Sodium carbonate | / | / | / | 14.5 | 13 | / |
| | Mass fraction of the active pharmaceutical ingredient/% | | 56 | 54.5 | 54.4 | 40 | 70 | 56 |
| | Mass fraction of the filler/% | | 19.5 | 10 | 30 | 30 | 10 | 19.5 |
| | Mass fraction of the disintegrant/% | | 8 | 12 | 5 | 12 | 5 | 8 |
| | Mass fraction of the lubricant/% | | 1 | 2 | 0.5 | 2 | 0.5 | 1 |
| | Mass fraction of the glidant/% | | 0.5 | 1.5 | 0.1 | 1.5 | 1.5 | 0.5 |
| | Mass fraction of the alkaline substance/% | | 15 | 20 | 10 | 14.5 | 13 | 15 |
| Second layer | Active pharmaceutical ingredient | 5-Nitro-8-hydroxyquinoline L-lysinate monohydrate | 56 | 51 | 59.8 | 40 | 70 | 56 |
| | Filler | Microcrystalline cellulose | / | / | / | 30 | / | / |
| | | Starch | / | / | / | / | 10 | / |
| | | Lactose monohydrate | 18 | 10 | 30 | / | / | / |
| | | Calcium hydrogen phosphate | / | / | / | / | / | 18 |
| | Sustained release material | Hydroxypropyl methylcellulose K4M | 25 | 35 | 10 | / | / | 25 |
| | | Xanthan gum | / | / | / | 26 | 19 | / |
| | Lubricant | Magnesium stearate | 0.5 | 2 | 0.1 | / | / | 0.5 |
| | | Stearic acid | / | / | / | 2 | / | / |
| | | Sodium dodecyl sulfate | / | / | / | / | 0.5 | / |
| | Glidant | Micronized silica gel | 0.5 | 2 | 0.1 | / | / | 0.5 |
| | | Talc | / | / | / | 2 | 0.5 | / |
| | Mass fraction of the active pharmaceutical ingredient/% | | 56 | 51 | 59.8 | 40 | 70 | 56 |
| | Mass fraction of the filler/% | | 18 | 10 | 30 | 30 | 10 | 18 |
| | Mass fraction of the sustained release material/% | | 25 | 35 | 10 | 26 | 19 | 25 |
| | Mass fraction of the lubricant/% | | 0.5 | 2 | 0.1 | 2 | 0.5 | 0.5 |
| | Mass fraction of the glidant/% | | 0.5 | 2 | 0.1 | 2 | 0.5 | 0.5 |
| Mass of the granules of the first layer in each tablet/mg | | | See the respective Examples | 166.67 | 333.33 | 250 | 250 | 250 |
| Mass of the granules of the second layer in each tablet/mg | | | | 333.33 | 166.67 | 250 | 250 | 250 |
| Ratio of the mass of the granules of the first layer to the mass of the granules of the second layer in each tablet | | | | 1:2 | 2:1 | 1:1 | 1:1 | 1:1 |
| Total number of tablets | | | 100 | 100 | 100 | 100 | 100 | 100 |

In the following Examples, the tableting machine is a TDP-6 single punch tableting machine (Shanghai Tianfan Machinery Factory).

Example 1

The active pharmaceutical ingredients and each auxiliary material were respectively passed through an 80-mesh sieve for later use.

Each component was accurately weighed according to the above formula of the first layer. 5-Nitro-8-hydroxyquinoline L-lysinate monohydrate, microcrystalline cellulose, crospovidone and sodium bicarbonate were thoroughly mixed, followed by the addition of 75 wt % ethanol in water (the 75 wt % ethanol in water was present in a conventional amount, i.e., in an amount of 10% to 30% by mass, relative to the total mass of the components of the first layer) to obtain a soft material. The soft material was passed through a 24-mesh sieve, dried in an air drying oven at 60° C. for 2 hours, milled with a 24-mesh sieve, followed by the addition of magnesium stearate and micronized silica gel, and mixed well to obtain the granules of the first layer.

Each component was accurately weighed according to the above formula of the second layer. 5-Nitro-8-hydroxyquinoline L-lysinate monohydrate, lactose monohydrate and hydroxypropyl methylcellulose K4M were thoroughly mixed, followed by the addition of 75 wt % ethanol in water (the 75 wt % ethanol in water was present in a conventional amount, i.e., in an amount of 10% to 30% by mass, relative to the total mass of the components of the second layer) to obtain a soft material. The soft material was passed through a 24-mesh sieve, dried in an air drying oven at 60° C. for 2 hours, milled with a 24-mesh sieve, followed by the addition of magnesium stearate and micronized silica gel, and mixed well to obtain the granules of the second layer.

250 mg of the granules of the first layer and the second layer were weighed respectively for later use (i.e., the mass ratio of the two was 1:1). The granules of the first layer were poured into the die ring of the tableting machine, and gently compressed to be flat as the first layer. The granules of the second layer were poured into the die ring of the tableting machine, and compressed on the top of the first layer to obtain the second layer, and the tablet of Example 1 was thus obtained. The punch diameter of the tableting machine was 11 mm, and the pressure was controlled at 60 to 80 N.

Example 2

The granules of the first layer and the granules of the second layer were prepared according to the method of Example 1.

166.67 mg of the granules of the first layer and 333.33 mg of the granules of the second layer were weighed for later use (i.e., the mass ratio of the two was 1:2). The granules of the second layer were poured into the die ring of the tableting machine, and gently compressed to be flat as the second layer. The granules of the first layer were poured into the die ring of the tableting machine, and compressed on the top of the second layer to obtain the first layer, and the tablet of Example 2 was thus obtained. The punch diameter of the tableting machine was 11 mm, and the pressure was controlled at 60 to 80 N.

Example 3

The granules of the first layer and the granules of the second layer were prepared according to the method of Example 1.

333.33 mg of the granules of the first layer and 166.67 mg of the granules of the second layer were weighed for later use (i.e., the mass ratio of the two was 2:1). The granules of the first layer were poured into the die ring of the tableting machine, and gently compressed to be flat as the first layer. The granules of the second layer were poured into the die ring of the tableting machine, and compressed on the top of the first layer to obtain the second layer, and the tablet of Example 3 was thus obtained. The punch diameter of the tableting machine was 11 mm, and the pressure was controlled at 60 to 80 N.

Example 4

The active pharmaceutical ingredients and each auxiliary material were respectively passed through an 80-mesh sieve for later use.

Each component was accurately weighed according to the above formula of the first layer. 5-Nitro-8-hydroxyquinoline L-lysinate monohydrate, microcrystalline cellulose, crospovidone and sodium bicarbonate were thoroughly mixed, followed by the addition of 75 wt % ethanol in water (the 75 wt % ethanol in water was present in a conventional amount, i.e., in an amount of 10% to 30% by mass, relative to the total mass of the components of the first layer) to obtain a soft material. The soft material was passed through a 24-mesh sieve, dried in an air drying oven at 60° C. for 2 hours, milled with a 24-mesh sieve, followed by the addition of magnesium stearate and micronized silica gel, and mixed well to obtain the granules of the first layer.

Each component was accurately weighed according to the above formula of the second layer. 5-Nitro-8-hydroxyquinoline L-lysinate monohydrate, lactose monohydrate and hydroxypropyl methylcellulose K4M were thoroughly mixed, followed by the addition of 75 wt % ethanol in water (the 75 wt % ethanol in water was present in a conventional amount, i.e., in an amount of 10% to 30% by mass, relative to the total mass of the components of the second layer) to obtain a soft material. The soft material was passed through a 24-mesh sieve, dried in an air drying oven at 60° C. for 2 hours, milled with a 24-mesh sieve, followed by the addition of magnesium stearate and micronized silica gel, and mixed well to obtain the granules of the second layer.

166.67 mg of the granules of the first layer and 333.33 mg of the granules of the second layer were weighed for later use (i.e., the mass ratio of the two was 1:2). The granules of the second layer were poured into the die ring of the tableting machine, and gently compressed to be flat as the second layer. The granules of the first layer were poured into the die ring of the tableting machine, and compressed on the top of the second layer to obtain the first layer, and the tablet of Example 4 was thus obtained. The punch diameter of the tableting machine was 11 mm, and the pressure was controlled at 60 to 80 N.

Example 5

The active pharmaceutical ingredients and each auxiliary material were respectively passed through an 80-mesh sieve for later use.

Each component was accurately weighed according to the above formula of the first layer. 5-Nitro-8-hydroxyquinoline L-lysinate monohydrate, microcrystalline cellulose, crospovidone and sodium bicarbonate were thoroughly mixed, followed by the addition of 75 wt % ethanol in water (the 75 wt % ethanol in water was present in a conventional amount, i.e., in an amount of 10% to 30% by mass, relative to the total mass of the components of the first layer) to obtain a soft material. The soft material was passed through a 24-mesh sieve, dried in an air drying oven at 60° C. for 2 hours, milled with a 24-mesh sieve, followed by the addition of magnesium stearate and micronized silica gel, and mixed well to obtain the granules of the first layer.

Each component was accurately weighed according to the above formula of the second layer. 5-Nitro-8-hydroxyquinoline L-lysinate monohydrate, lactose monohydrate and hydroxypropyl methylcellulose K4M were thoroughly mixed, followed by the addition of 75 wt % ethanol in water (the 75 wt % ethanol in water was present in a conventional amount, i.e., in an amount of 10% to 30% by mass, relative to the total mass of the components of the second layer) to obtain a soft material. The soft material was passed through a 24-mesh sieve, dried in an air drying oven at 60° C. for 2 hours, milled with a 24-mesh sieve, followed by the addition of magnesium stearate and micronized silica gel, and mixed well to obtain the granules of the second layer.

333.33 mg of the granules of the first layer and 166.67 mg of the granules of the second layer were weighed for later use (i.e., the mass ratio of the two was 2:1). The granules of the first layer were poured into the die ring of the tableting machine, and gently compressed to be flat as the first layer. The granules of the second layer were poured into the die ring of the tableting machine, and compressed on the top of the first layer to obtain the second layer, and the tablet of Example 5 was thus obtained. The punch diameter of the tableting machine was 11 mm, and the pressure was controlled at 60 to 80 N.

Example 6

The active pharmaceutical ingredients and each auxiliary material were respectively passed through an 80-mesh sieve for later use.

Each component was accurately weighed according to the above formula of the first layer. 5-Nitro-8-hydroxyquinoline L-lysinate monohydrate, lactose monohydrate, low-substituted hydroxypropyl cellulose and sodium carbonate were thoroughly mixed, followed by the addition of 75 wt % ethanol in water (the 75 wt % ethanol in water was present in a conventional amount, i.e., in an amount of 10% to 30% by mass, relative to the total mass of the components of the first layer) to obtain a soft material. The soft material was passed through a 24-mesh sieve, dried in an air drying oven at 60° C. for 2 hours, milled with a 24-mesh sieve, followed by the addition of sodium lauryl sulfate and talc, and mixed well to obtain the granules of the first layer.

Each component was accurately weighed according to the above formula of the second layer. 5-Nitro-8-hydroxyquinoline L-lysinate monohydrate, microcrystalline cellulose and xanthan gum were thoroughly mixed, followed by the addition of 75 wt % ethanol in water (the 75 wt % ethanol in water was present in a conventional amount, i.e., in an amount of 10% to 30% by mass, relative to the total mass of the components of the second layer) to obtain a soft material. The soft material was passed through a 24-mesh sieve, dried in an air drying oven at 60° C. for 2 hours, milled with a 24-mesh sieve, followed by the addition of stearic acid and talc, and mixed well to obtain the granules of the second layer.

250 mg of the granules of the first layer and 250 mg of the granules of the second layer were weighed for later use (i.e., the mass ratio of the two was 1:1). The granules of the first layer were poured into the die ring of the tableting machine, and gently compressed to be flat as the first layer. The granules of the second layer were poured into the die ring of the tableting machine, and compressed on the top of the first layer to obtain the second layer, and the tablet of Example 6 was thus obtained. The punch diameter of the tableting machine was 11 mm, and the pressure was controlled at 60 to 80 N.

Example 7

The active pharmaceutical ingredients and each auxiliary material were respectively passed through an 80-mesh sieve for later use.

Each component was accurately weighed according to the above formula of the first layer. 5-Nitro-8-hydroxyquinoline L-lysinate monohydrate, starch, sodium carboxymethyl starch and sodium carbonate were thoroughly mixed, followed by the addition of 75 wt % ethanol in water (the 75 wt % ethanol in water was present in a conventional amount, i.e., in an amount of 10% to 30% by mass, relative to the total mass of the components of the first layer) to obtain a soft material. The soft material was passed through a 24-mesh sieve, dried in an air drying oven at 60° C. for 2 hours, milled with a 24-mesh sieve, followed by the addition of stearic acid and talc, and mixed well to obtain the granules of the first layer.

Each component was accurately weighed according to the above formula of the second layer. 5-Nitro-8-hydroxyquinoline L-lysinate monohydrate, starch and xanthan gum were thoroughly mixed, followed by the addition of 75 wt % ethanol in water (the 75 wt % ethanol in water was present in a conventional amount, i.e., in an amount of 10% to 30% by mass, relative to the total mass of the components of the second layer) to obtain a soft material. The soft material was passed through a 24-mesh sieve, dried in an air drying oven at 60° C. for 2 hours, milled with a 24-mesh sieve, followed by the addition of sodium lauryl sulfate and talc, and mixed well to obtain the granules of the second layer.

250 mg of the granules of the first layer and 250 mg of the granules of the second layer were weighed for later use (i.e., the mass ratio of the two was 1:1). The granules of the first layer were poured into the die ring of the tableting machine, and gently compressed to be flat as the first layer. The granules of the second layer were poured into the die ring of the tableting machine, and compressed on the top of the first layer to obtain the second layer, and the tablet of Example 7 was thus obtained. The punch diameter of the tableting machine was 11 mm, and the pressure was controlled at 60 to 80 N.

Example 8

The active pharmaceutical ingredients and each auxiliary material were respectively passed through an 80-mesh sieve for later use.

Each component was accurately weighed according to the above formula of the first layer. 5-Nitro-8-hydroxyquinoline L-lysinate monohydrate, calcium hydrogen phosphate, croscarmellose sodium and sodium bicarbonate were thoroughly mixed, followed by the addition of 75 wt % ethanol in water (the 75 wt % ethanol in water was present in a conventional amount, i.e., in an amount of 10% to 30% by mass, relative to the total mass of the components of the first layer) to obtain a soft material. The soft material was passed through a 24-mesh sieve, dried in an air drying oven at 60° C. for 2 hours, milled with a 24-mesh sieve, followed by the addition of magnesium stearate and micronized silica gel, and mixed well to obtain the granules of the first layer.

Each component was accurately weighed according to the above formula of the second layer. 5-Nitro-8-hydroxyquinoline L-lysinate monohydrate, calcium hydrogen phosphate and hydroxypropyl methylcellulose K4M were thoroughly mixed, followed by the addition of 75 wt % ethanol in water (the 75 wt % ethanol in water was present in a conventional amount, i.e., in an amount of 10% to 30% by mass, relative to the total mass of the components of the second layer) to obtain a soft material. The soft material was passed through a 24-mesh sieve, dried in an air drying oven at 60° C. for 2 hours, milled with a 24-mesh sieve, followed by the addition of magnesium stearate and micronized silica gel, and mixed well to obtain the granules of the second layer.

250 mg of the granules of the first layer and 250 mg of the granules of the second layer were weighed for later use (i.e., the mass ratio of the two was 1:1). The granules of the first layer were poured into the die ring of the tableting machine, and gently compressed to be flat as the first layer. The granules of the second layer were poured into the die ring of the tableting machine, and compressed on the top of the first layer to obtain the second layer, and the tablet of Example 8 was thus obtained. The punch diameter of the tableting machine was 11 mm, and the pressure was controlled at 60 to 80 N.

Test Example 1 Dissolution Rate (1) Selection of Dissolution Medium

The solubility of the main drug (5-nitro-8-hydroxyquinoline L-lysinate monohydrate) is greatly affected by pH. In order to select a suitable dissolution medium to achieve the sink condition, the saturated solubility of the main drug in water, pH 1.0 hydrochloric acid solution, pH 4.0 buffer (solution A: water was added to 21 g of citric acid or 19.2 g of anhydrous citric acid to obtain a 1000 mL solution, which was then stored in a refrigerator; solution B: water was added to 71.63 g of disodium hydrogen phosphate to obtain a 1000 mL solution; 61.45 mL of solution A and 38.55 mL of solution B were mixed and shaked well to obtain the pH 4.0 buffer) and pH 6.8 PBS buffer (118 mL of 0.2 mol/L sodium hydroxide solution was added to 250 mL of 0.2 mol/L phosphoric acid solution, the resulting solution was diluted with water to 1000 mL and shaked well to obtain the pH 6.8 PBS buffer) were investigated. The specific method: excessive main drug (about 1.5 g) was added to 10 mL of the above four media, respectively; the resulting mixture was placed in a SHA-B multifunctional water bath constant temperature shaker (manufacturer: Zenith Lab (Jiangsu) Co., Ltd.) at water bath temperature of 37° C. and shaked at a speed of 280 rpm for 72 hours; the solution was filtered through a 0.45 μm nitrocellulose membrane (manufacturer: Tianjin Jinteng Experimental Equipment Co., Ltd.); and the filtrate was measured with a UV-2700 ultraviolet-visible spectrophotometer (manufacturer: Shimadzu, Japan), detection wavelength: 369 nm. The results are shown in Table 1 below.

TABLE 1

Saturated solubility of the main drug in different media

| Medium | Saturated solubility (mg/ml) | Whether the sink condition was achieved |
|---|---|---|
| Water | 100.5 | Yes |
| pH 1.0 hydrochloric acid solution | 1.54 | Yes |
| pH 4.0 buffer | 0.43 | No |
| pH 6.8 PBS buffer | 15.7 | Yes |

The results showed that the sink condition could not be achieved in pH 4.0 buffer. Therefore, pH 1.0 hydrochloric acid solution, water and pH 6.8 PBS buffer can be selected as the dissolution media.

(2) Selection of Dissolution Condition

Figure 2:
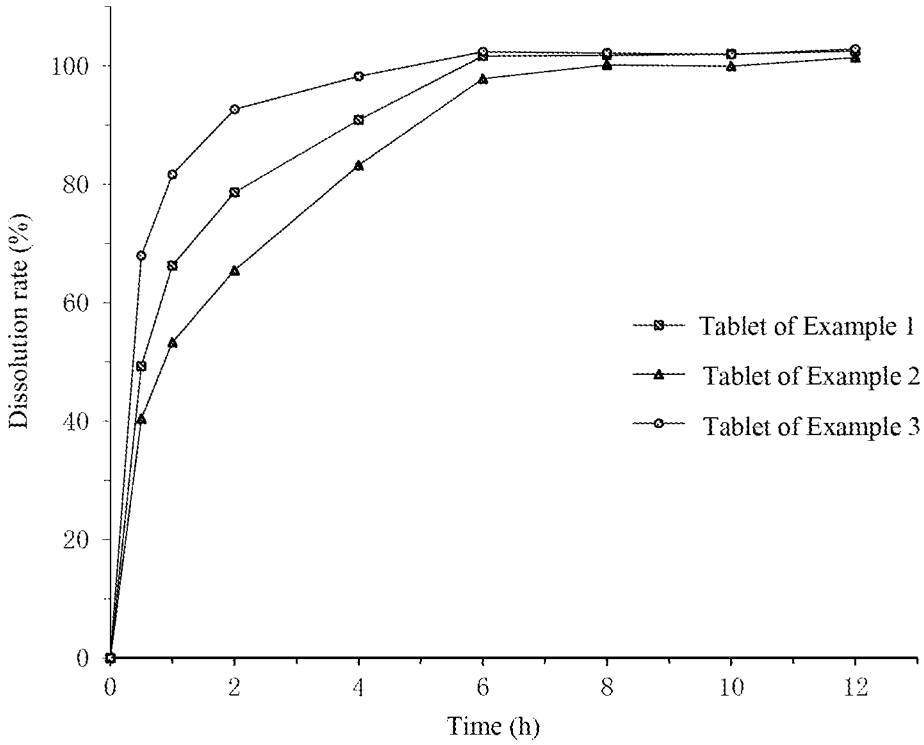
FIG. 2 is the dissolution profile of the tablets prepared in Examples 1 to 3 in water.

The dissolution rate was determined with reference to the basket method described in Chinese Pharmacopoeia at a speed of 100 rpm. The dissolution medium was pH 6.8 PBS buffer or water, and the volume of the dissolution medium was 900 mL at 37° C. One tablet of Examples 1 to 3 were added into the dissolution vessel, respectively. 10 mL of the dissolution solution was taken at the time shown in Table 2 or 3 below, and then 10 mL of pH 6.8 PBS buffer or water having the same temperature was supplemented. The obtained dissolution solution was diluted by an appropriate fold (10- or 20-fold) (according to the data in Table 2 and Table 3, generally, 10-fold dilution was carried out at the first time point, and 20-fold dilution was carried out at the subsequent time points), and the UV absorbance of the resulting solution was measured. The dissolution percent was calculated, and the dissolution profile was plotted as shown in FIGS. 1 and 2. The dissolution rate results are shown in Table 2 and Table 3 below.

Figure 3:
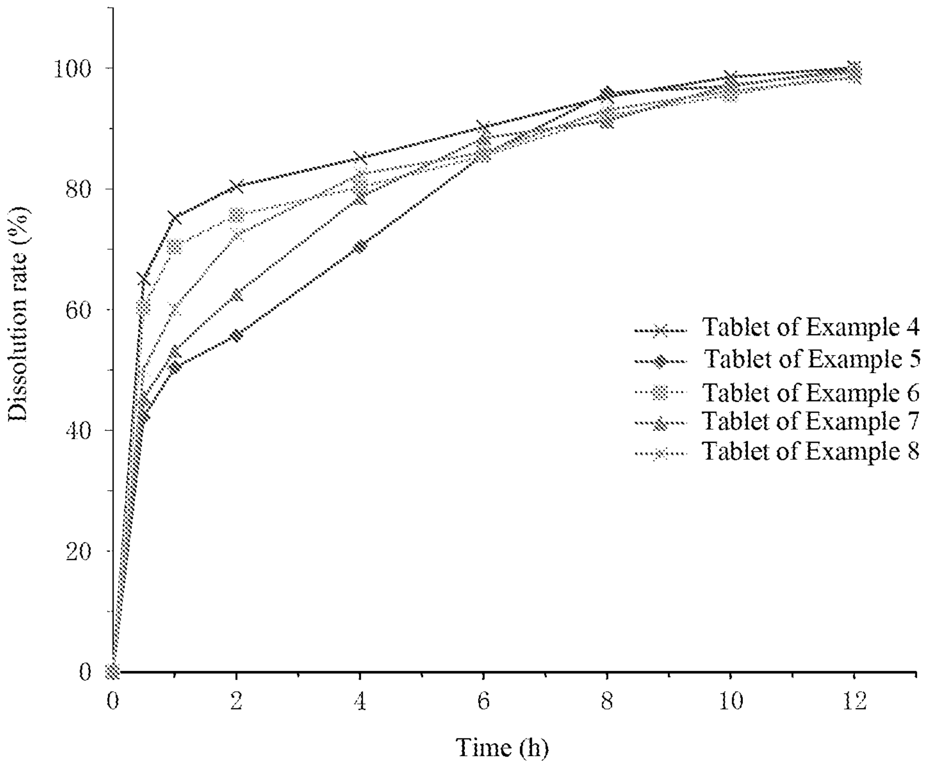
FIG. 3 is the dissolution profile of the tablets prepared in Examples 4 to 8 in water.

The dissolution rate was determined with reference to the basket method described in Chinese Pharmacopoeia at a speed of 100 rpm. The dissolution medium was water, and the volume of the dissolution medium was 900 mL at 37° C. One tablet of Examples 4 to 8 were added into the dissolution vessel, respectively. 10 mL of the dissolution solution was taken at the time shown in Table 4 below, and then 10 mL of water having the same temperature was supplemented. The obtained dissolution solution was diluted by an appropriate fold (10- or 20-fold) (according to the data in Table 4, generally, 10-fold dilution was carried out at the first time point, and 20-fold dilution was carried out at the subsequent time points), and the UV absorbance of the resulting solution was measured. The dissolution percent was calculated, and the dissolution profile was plotted as shown in FIG. 3. The dissolution rate results are shown in Table 4 below.

(3) Dissolution Rate Results

TABLE 2

Dissolution rate results of the tablet of Examples 1 to 3 in pH 6.8 PBS buffer

| | Average dissolution rate (n = 3) | SD |
|---|---|---|
| Tablet of Example 1 | | |
| 0.5 h | 53.93% | 1.53% |
| 1 h | 59.15% | 1.03% |
| 2 h | 69.63% | 2.30% |
| 4 h | 79.46% | 3.00% |
| 6 h | 87.53% | 2.22% |
| 8 h | 93.71% | 2.00% |
| 10 h | 95.35% | 2.16% |
| 12 h | 97.58% | 2.56% |
| Tablet of Example 3 | | |
| 0.5 h | 69.86% | 2.36% |
| 1 h | 79.31% | 3.04% |
| 2 h | 88.92% | 2.84% |
| 4 h | 95.89% | 0.83% |
| 6 h | 98.20% | 0.11% |
| 8 h | 100.00% | 1.70% |
| 10 h | 100.34% | 1.93% |
| 12 h | 101.84% | 0.32% |
| Tablet of Example 2 | | |
| 0.5 h | 40.17% | 2.31% |
| 1 h | 44.41% | 2.85% |
| 2 h | 52.32% | 2.33% |
| 4 h | 65.76% | 2.55% |
| 6 h | 75.45% | 1.30% |
| 8 h | 87.77% | 2.32% |
| 10 h | 92.41% | 2.36% |
| 12 h | 96.99% | 2.33% |

TABLE 3

Dissolution rate results of the tablet of Examples 1 to 3 in water

| | Average dissolution rate (n = 3) | SD |
|---|---|---|
| Tablet of Example 1 | | |
| 0.5 h | 49.26% | 2.67% |
| 1 h | 66.28% | 0.43% |
| 2 h | 78.61% | 2.83% |
| 4 h | 90.87% | 1.99% |
| 6 h | 101.64% | 0.28% |
| 8 h | 101.78% | 0.21% |
| 10 h | 102.00% | 0.40% |
| 12 h | 102.50% | 0.43% |
| Tablet of Example 3 | | |
| 0.5 h | 67.94% | 2.05% |
| 1 h | 81.63% | 0.58% |
| 2 h | 92.65% | 2.10% |
| 4 h | 98.22% | 1.08% |
| 6 h | 102.36% | 1.05% |
| 8 h | 102.16% | 1.83% |
| 10 h | 101.90% | 1.77% |
| 12 h | 102.82% | 1.32% |
| Tablet of Example 2 | | |
| 0.5 h | 40.39% | 2.71% |
| 1 h | 53.30% | 1.81% |

TABLE 3-continued

Dissolution rate results of the tablet of Examples 1 to 3 in water

| | Average dissolution rate (n = 3) | SD |
|---|---|---|
| 2 h | 65.46% | 2.03% |
| 4 h | 83.21% | 1.51% |
| 6 h | 97.82% | 3.25% |
| 8 h | 100.16% | 1.24% |
| 10 h | 99.94% | 0.03% |
| 12 h | 101.40% | 1.34% |

TABLE 4

Dissolution rate results of the tablet of Examples 4 to 8 in water

| | Average dissolution rate (n = 3) | SD % |
|---|---|---|
| Tablet of Example 4 | | |
| 0.5 h | 65.12% | 1.67% |
| 1 h | 75.23% | 0.42% |
| 2 h | 80.41% | 0.83% |
| 4 h | 85.10% | 1.44% |
| 6 h | 90.22% | 0.21% |
| 8 h | 95.24% | 0.27% |
| 10 h | 98.52% | 0.42% |
| 12 h | 100.08% | 0.13% |
| Tablet of Example 5 | | |
| 0.5 h | 42.21% | 2.08% |
| 1 h | 50.35% | 0.51% |
| 2 h | 55.71% | 1.1% |
| 4 h | 70.42% | 1.01% |
| 6 h | 85.61% | 0.35% |
| 8 h | 95.91% | 0.87% |
| 10 h | 97.02% | 0.77% |
| 12 h | 99.88% | 0.35% |
| Tablet of Example 6 | | |
| 0.5 h | 60.33% | 2.75% |
| 1 h | 70.45% | 0.81% |
| 2 h | 75.62% | 1.03% |
| 4 h | 80.27% | 1.52% |
| 6 h | 85.44% | 2.25% |
| 8 h | 92.09% | 1.21% |
| 10 h | 95.55% | 0.63% |
| 12 h | 99.34% | 0.34% |
| Tablet of Example 7 | | |
| 0.5 h | 45.33% | 2.87% |
| 1 h | 53.19% | 0.47% |
| 2 h | 62.62% | 1.83% |
| 4 h | 78.61% | 1.02% |
| 6 h | 88.42% | 0.29% |
| 8 h | 91.28% | 0.27% |
| 10 h | 97.19% | 0.24% |
| 12 h | 99.52% | 0.23% |
| Tablet of Example 8 | | |
| 0.5 h | 50.11% | 2.77% |
| 1 h | 60.18% | 1.43% |
| 2 h | 72.33% | 0.83% |
| 4 h | 82.41% | 1.03% |
| 6 h | 86.05% | 0.55% |
| 8 h | 93.06% | 0.32% |
| 10 h | 96.22% | 0.26% |
| 12 h | 98.43% | 0.33% |

It can be seen from the experimental results in Tables 2 and 3 and FIGS. 1 and 2 that in water or pH 6.8 PBS buffer, there are differences in the dissolution profiles of tablets with different mass ratios of the first layer to the second layer. The dissolution rate of the tablet of Example 3 (the mass ratio of the first layer to the second layer is 2:1) at 1 h reaches 80%. The dissolution rate of the tablet of Example 1 (the mass ratio of the first layer to the second layer is 1:1) at 4 h reaches 80%. The dissolution rate of the tablet of Example 2 (the mass ratio of the first layer to the second layer is 1:2) at 8 hour reaches 80%. The burst release in the early stage (within 0 to 2 h) increases with the increase of the proportion of the first layer. It can be seen from the dissolution profile that in the early stage of the dissolution (within 0 to 2 h), the burst release of the three is obvious, and the difference is significant. In the later stage (within 2 to 8 h), they all show a good sustained-release effect. This is in line with the intention of the sustained-release double-layer tablet design, and basically achieves the effect of the combination of sustained-release and immediate-release in vitro.

It can be seen from Table 4 and FIG. 3 that the in vitro dissolution profiles of the tablets of Examples 4 to 8 are basically the same as those of the tablets of Examples 1 to 3. The first layer of the drug is rapidly released in the early stage (within 0 to 2 h), and can achieve a rapid treatment effect. The second layer of the drug is slowly released in the later stage (within 2 to 8 h), and can maintain the treatment effect. This is in line with the intention of the sustained-release double-layer tablet design, and basically achieves the effect of the combination of sustained-release and immediate-release in vitro.

Test Example 2 Pharmacokinetics Test in Beagle Dogs

Experimental Design:

The tablets prepared in Examples 1 to 3 were orally administered to three qualified healthy beagle dogs (purchased from Beijing Marshall Biotechnology Co., Ltd., 10 to 12 kg, 13 to 15 months old). The tested beagle dogs were fasted before the experiment, and had free access to water. The experiment was carried out in 4 cycles, one formulation was administered in each cycle, one tablet was administered to each beagle dog, and each cycle was separated by a recovery period of 2 to 3 days. 2 mL of whole blood was collected from the anterior/hind extremity veins at 0 minute before the administration and 0.25, 0.5, 1, 2, 4, 6, 8, 10, 12, 16 and 24 hours after the administration, placed in a 5 mL centrifuge tube containing EDTA-K2 anticoagulant (manufacturer: Guangzhou Bangbiao Medical Equipment Co., Ltd.), mixed immediately and centrifuged at 5000 rpm for 5 minutes. 400 μL of plasma was taken and placed in another clean centrifuge tube, and stored in a −20° C. refrigerator for later test.

Test samples: tablets prepared in Examples 1 to 3. Reference formulation: 500 mg of the granules of the first layer prepared in Example 1 were poured into the die ring of the tableting machine, and compressed to obtain the reference formulation, the punch diameter was 11 mm, and the pressure was controlled at 60 to 80 N.

Sample Test:

Instruments: Agilent 1200 liquid chromatography, AB SCIEX API4000 tandem quadrupole mass spectrometer.

Acetonitrile, methanol, and formic acid were purchased from Dikma Technologies Inc., and other reagents were chromatographic grade.

Liquid Chromatography Conditions:

Mobile phase: A: methanol-water-formic acid (10:90:0.1, v/v/v), B: methanol-formic acid (100:0.1, v/v)

| Gradient elution: | | |
|---|---|---|
| Time (min) | A % | B % |
| 0.00 | 70.0 | 30.0 |
| 2.00 | 10.0 | 90.0 |
| 4.00 | 10.0 | 90.0 |
| 4.01 | 70.0 | 30.0 |
| 6.00 | 70.0 | 30.0 |

Flow rate: 0.40 mL/min

Injection volume: 10 μL

Mass spectrometry conditions:

Ion source: Turbo Ionspray ($ESI^+$);

Detection mode: MRM;

Ion source related parameters: GS1 (gas 1, psi): 50, GS2 (gas 2, psi): 50, TEM (temperature, ° C.): 450, CUR (curtain gas, psi): 30, IS (spray voltage, V): 5000, CAD (collision gas, psi): 5, the (interface heater): on.

TABLE 5

Pharmacokinetic test results of the tablets of Examples 1 to 3

| Example | Mass ratio of the first layer to the second layer | $T_{max}$ (h) | $C_{max}$ (ng/mL) | $AUG_{0-\infty}$ (h · ng/mL) | $t_{1/2}$(h) | Relative bioavailability F(%) |
|---|---|---|---|---|---|---|
| 2 | 1:2 | 1.00 ± 0 | 1775 ± 219 | 5039 ± 848 | 6.39 ± 0.52 | 84.4 |
| 1 | 1:1 | 1.17 ± 0.76 | 2820 ± 1133 | 6677 ± 2277 | 3.89 ± 0.71 | 111.8 |
| 3 | 2:1 | 0.58 ± 0.38 | 3730 ± 1559 | 6885 ± 1931 | 3.29 ± 1.62 | 115.3 |
| Reference formulation | Immediate-release tablet | 0.83 ± 0.29 | 3607 ± 1099 | 5972 ± 1116 | 3.98 ± 2.57 | 100 |

It can be seen from the above Table 5 that the tablets of Examples 1 to 3 and the reference formulation are both bioequivalent in beagle dogs (F value ranges from 80% to 120%). Moreover, the plasma concentration $C_{max}$ of the tablets of Example 1 and Example 2 is lower than that of the reference formulation, which can reduce the occurrence of side effects; the plasma concentration $C_{max}$ of the tablet of Example 2 is significantly lower, the half-life $t_{1/2}$ is significantly longer, and the sustained-release effect is excellent.

What is claimed is:

1. A nitroxoline lysinate-containing pharmaceutical composition, characterized in that it comprises a first layer and a second layer; the first layer comprises 40% to 70% of an active pharmaceutical ingredient, 10% to 30% of a filler, 5% to 12% of a disintegrant, 0.5% to 2% of a lubricant, 0.1% to 1.5% of a glidant and 10% to 20% of an alkaline substance by weight, relative to the total weight of the first layer;

wherein, the filler in the first layer is microcrystalline cellulose; the disintegrant in the first layer is crospovidone; the lubricant in the first layer is magnesium stearate; the glidant in the first layer is micronized silica gel; and the alkaline substance in the first layer is one or two selected from the group consisting of sodium bicarbonate and sodium carbonate;

the second layer comprises 40% to 70% of an active pharmaceutical ingredient, 10% to 30% of a filler, 10% to 35% of a sustained release material, 0.1% to 2% of a lubricant and 0.1% to 2% of a glidant by weight, relative to the total weight of the second layer;

wherein, the filler in the second layer is lactose monohydrate; the sustained release material in the second layer is hydroxypropyl methylcellulose K4M; the lubricant in the second layer is magnesium stearate; and the glidant in the second layer is micronized silica gel; and each of the active pharmaceutical ingredient in the first layer and the active pharmaceutical ingredient in the second layer is one or more independently selected from the group consisting of nitroxoline lysinate, a crystal form of nitroxoline lysinate, and a solvate of nitroxoline lysinate; and the mass ratio of the first layer to the second layer is 1:3 to 1:1.5.

2. The nitroxoline lysinate-containing pharmaceutical composition according to claim 1, characterized in that each of the active pharmaceutical ingredient in the first layer and the active pharmaceutical ingredient in the second layer is a hydrate of nitroxoline lysinate;

the active pharmaceutical ingredient in the first layer is present in an amount of 40% to 60% by mass, relative to the mass of the first layer;

the filler in the first layer is present in an amount of 15% to 30% by mass, relative to the mass of the first layer;

the disintegrant in the first layer is present in an amount of 7% to 12% by mass, relative to the mass of the first layer;

the lubricant in the first layer is present in an amount of 0.5% to 1.5% by mass, relative to the mass of the first layer;

the glidant in the first layer is present in an amount of 0.2% to 1% by mass, relative to the mass of the first layer;

and, the alkaline substance in the first layer is present in an amount of 14% to 20% by mass, relative to the mass of the first layer.

3. The nitroxoline lysinate-containing pharmaceutical composition according to claim 1, characterized in that the active pharmaceutical ingredient in the second layer is present in an amount of 50% to 60% by mass, relative to the mass of the second layer;

the filler in the second layer is present in an amount of 16% to 30% by mass, relative to the mass of the second layer;

the sustained release material in the second layer is present in an amount of 19% to 35% by mass, relative to the mass of the second layer;

the lubricant in the second layer is present in an amount of 0.2% to 1% by mass, relative to the mass of the second layer;

and, the glidant in the second layer is present in an amount of 0.2% to 1% by mass, relative to the mass of the second layer.

4. The nitroxoline lysinate-containing pharmaceutical composition according to claim 1, characterized in that the mass ratio of the first layer to the second layer is 1:2-1:1.5.

5. The nitroxoline lysinate-containing pharmaceutical composition according to claim 1, characterized in that the pharmaceutical composition further comprises a coating agent.

6. The nitroxoline lysinate-containing pharmaceutical composition according to claim 1, characterized in that the pharmaceutical composition further comprises one or more of colorant, pH adjuster, surfactant, stabilizer and fragrance.

7. The nitroxoline lysinate-containing pharmaceutical composition according to claim 1, characterized in that the pharmaceutical composition is a solid formulation.

8. A nitroxoline lysinate-containing formulation, characterized in that it comprises a first layer and a second layer;

the first layer comprises 40% to 60% of an active pharmaceutical ingredient, 15% to 30% of a filler, 7% to 12% of a disintegrant, 0.5% to 1.5% of a lubricant, 0.2% to 1% of a glidant and 14% to 20% of an alkaline substance by weight, relative to the total weight of the first layer;

the second layer comprises 50% to 60% of an active pharmaceutical ingredient, 16% to 30% of a filler, 19% to 35% of a sustained release material, 0.2% to 1% of a lubricant and 0.2% to 1% of a glidant by weight, relative to the total weight of the second layer; and each of the active pharmaceutical ingredient in the first layer and the active ingredient in the second layer is one or more independently selected from the group consisting of nitroxoline lysinate, a crystal form of nitroxoline lysinate, and a solvate of nitroxoline lysinate, the pharmaceutical composition is a sustained release tablet;

in the first layer, the filler is microcrystalline cellulose, the disintegrant is crospovidone, the lubricant is magnesium stearate, the glidant is micronized silica gel, and the alkaline substance is sodium bicarbonate; in the second layer, the filler is lactose monohydrate, the sustained release material is hydroxypropyl methylcellulose K4M, the lubricant is magnesium stearate, and the glidant is micronized silica gel; and the mass ratio of the first layer to the second layer is 1:3 to 1:1.5.

9. A method for preparing the nitroxoline lysinate-containing pharmaceutical composition according to claim 1, characterized in that it comprises the following steps of:

1) Mixing the remaining components of the first layer except the lubricant and the glidant, and subjecting the resulting mixture to wet granulation to obtain granule I; mixing the granule I with the lubricant and the glidant of the first layer to obtain the granules of the first layer;

2) Mixing the remaining components of the second layer except the lubricant and the glidant, and subjecting the resulting mixture to wet granulation to obtain granule II; mixing the granule II with the lubricant and the glidant of the second layer to obtain the granules of the second layer;

3) Compressing the granules of the first layer to obtain the first layer, and compressing the granules of the second layer on the top of the first layer to obtain the pharmaceutical composition; or, compressing the granules of the second layer to obtain the second layer, and compressing the granules of the first layer on the top of the second layer to obtain the pharmaceutical composition.

10. A method of treating an infectious disease or cancer in a subject in need thereof, the method comprising administering to the subject a therapeutically effective amount of the nitroxoline lysinate-containing pharmaceutical composition according to claim 1.

11. The method according to claim 10, wherein the infectious disease is urinary tract infection, and the cancer is bladder cancer.

12. A method of treating an infectious disease or cancer in a subject in need thereof, the method comprising administering to the subject a therapeutically effective amount of the nitroxoline lysinate-containing pharmaceutical composition according to claim 8.

13. The method according to claim 12, wherein the infectious disease is urinary tract infection, and the cancer is bladder cancer.

14. The nitroxoline lysinate-containing pharmaceutical composition according to claim 5, wherein the coating agent is Opadry.

15. The nitroxoline lysinate-containing pharmaceutical composition according to claim 5, wherein the ratio of the mass of the coating agent to the mass of the uncoated pharmaceutical composition is 2% to 4%.

16. The nitroxoline lysinate-containing pharmaceutical composition according to claim 7, wherein the solid formulation is a granule, powder or tablet.

17. The nitroxoline lysinate-containing formulation according to claim 8, wherein the mass ratio of the first layer to the second layer is 1:2-1:1.5.

18. The method according to claim 9, wherein the wet granulation process comprises mixing the remaining components of the first or the second layer except the lubricant and the glidant with ethanol in water to obtain a soft material, sieving, drying and milling; and the mass fraction of the ethanol in water is 70 wt % to 80 wt %.

19. The nitroxoline lysinate-containing formulation according to claim 8, wherein the active pharmaceutical ingredient in the first layer and the second layer is a hydrate of nitroxoline lysinate.

20. The nitroxoline lysinate-containing formulation according to claim 8, wherein the active pharmaceutical ingredient in the first layer and the second layer is nitroxoline lysinate monohydrate.

* * * * *